United States Patent [19]

Hoelderich et al.

[11] 4,433,188
[45] Feb. 21, 1984

[54] PREPARATION OF OLEFINS FROM METHANOL AND/OR DIMETHYL ETHER

[75] Inventors: Wolfgang Hoelderich; Wolf D. Mross, both of Frankenthal; Matthias Schwarzmann, Limburgerhof, all of Fed. Rep. of Germany

[73] Assignee: BASF Aktiengesellschaft, Fed. Rep. of Germany

[21] Appl. No.: 413,814

[22] Filed: Sep. 1, 1982

[30] Foreign Application Priority Data

Sep. 9, 1981 [DE] Fed. Rep. of Germany ....... 3135618

[51] Int. Cl.$^3$ ................................................ C07C 1/20
[52] U.S. Cl. .................................... 585/640; 585/312; 585/315; 585/357; 585/408; 585/469; 585/638; 585/733
[58] Field of Search ................... 585/25 M, 310, 312, 585/315, 357, 733, 638, 639, 640, 408, 409, 469

[56] References Cited

U.S. PATENT DOCUMENTS 4,025,576  5/1977  Chang et al. ........................ 585/640
4,052,472 10/1977  Givens et al. ....................... 585/640
4,058,576 11/1977  Chang et al. ........................ 585/640
4,292,458  9/1981  Klotz ................................... 585/640

FOREIGN PATENT DOCUMENTS 2615150 10/1976  Fed. Rep. of Germany .
2060684  5/1981  United Kingdom .

Primary Examiner—Delbert E. Gantz
Assistant Examiner—A. Pal
Attorney, Agent, or Firm—Keil & Witherspoon

[57] ABSTRACT

A process for the preparation of lower olefins from methanol or dimethyl ether by catalytic conversion at from 300° to 550° C. in two stages over borosilicate zeolites, wherein $C_2$–$C_4$-olefins and $C_1$–$C_4$-paraffins are removed after the first reaction stage, the $C_5{}^+$ hydrocarbons are passed to the second reaction stage, the aromatics are removed from the reaction product of the second stage and the remaining reaction products are recycled. The advantage of this process is an improvement in the yield of olefins.

10 Claims, 1 Drawing Figure

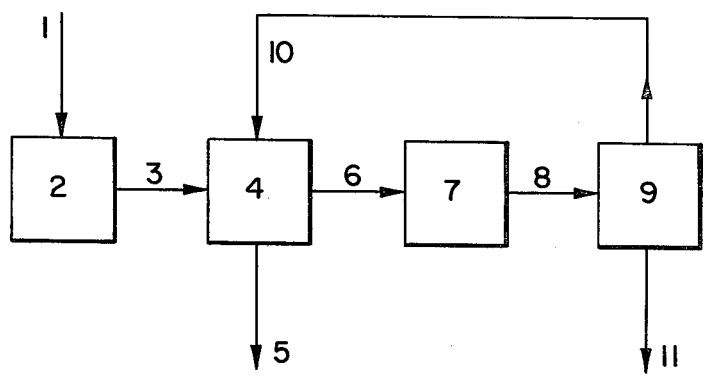

PREPARATION OF OLEFINS FROM METHANOL AND/OR DIMETHYL ETHER

A number of processes have been disclosed for the preparation of lower olefins from methanol and/or dimethyl ether.

Efforts to use methanol for the preparation of olefins have recently become of increasing interest. Methanol can be prepared from coal, by gasification and the preparation of synthesis gas by conversion, with the aid of proven techniques. If it proves possible to convert methanol into lower olefins in a technically simple manner, the methods of further processing which are customary today can be retained, as can the use of coal as the raw material. A number of processes for the preparation of olefins from methanol and/or dimethyl ether have therefore been developed in the past years. German Laid-Open Application DOS No. 2,615,150, for example, discloses such a process, in which the aluminosilicate zeolite ZMS-5 is used as the catalyst. However, all the processes which have hitherto been disclosed have the disadvantage that they are not economical, either because of the low conversion of methanol or because of the low olefin content in the case of a one-stage procedure. Under reaction conditions which can easily be realized in industry, the conventional zeolite catalysts of the pentasil type mainly give liquid hydrocarbons.

We have now found that the above disadvantages in the preparation of lower olefins from methanol and/or dimethyl ether by catalytic conversion at from 300° to 550° C. in the presence of zeolite catalysts can be avoided if the reaction is carried out over the catalyst in two stages, $C_2$–$C_4$-olefins and $C_1$–$C_4$-paraffins, or only the ethylene and propylene, being removed after the first reaction stage, the $C_5^+$ hydrocarbons, or these, the butenes and the $C_1$–$C_4$-paraffins, being passed to the second reaction stage, the aromatics being removed from the reaction product of the second stage and the remaining reaction products being recycled.

Borosilicate zeolites are particularly suitable for the process according to the invention.

In a particular embodiment, after removal of the aromatics, the reaction product from the second stage is recycled to the working up stage which follows the first reaction, and the $C_2$–$C_4$-olefins contained in the product are removed in this working up stage, together with the $C_2$–$C_4$-olefins from the first reaction stage, and the remaining hydrocarbons are passed to the second reaction stage.

The substantial advance of the process according to the invention is that, as a result of the procedure, after removal of the small aromatic content after the second process stage, all the other components are recycled, and processed to give the desired $C_2$–$C_4$-olefins. The use of borosilicate zeolites as catalysts for the conversion in both stages is particularly responsible for this advance towards higher $C_2$–$C_4$-olefin yields. In contrast to other catalysts for converting methanol, the borosilicate catalysts suppress the formation of aromatics. The higher aliphatics formed at this point can be further reacted in the second stage to give lower olefins.

We have also found that the catalytic conversion of methanol and/or dimethyl ether is particularly advantageously carried out at from 350° to 425° in the first reaction stage, since the aromatic content of the $C_5^+$ hydrocarbon fraction is thereby reduced in favor of the aliphatics. Another advantage of this preferred embodiment of the process is that the life of the catalysts used, which depends on temperature and throughput, is optimum in the range from 350° to 425° C. at a constant throughput.

The process scheme shown in the drawing (FIG. 1) illustrates the fundamental course of the process. The starting materials methanol and/or dimethyl ether pass from line (1) into the first reactor (2) of the two-stage process, where conversion of methanol and/or dimethyl ether into a hydrocarbon mixture is effected over a zeolite catalyst. The reaction products, which contain $C_2$–$C_4$-olefins, $C_1$–$C_4$-paraffins, liquid hydrocarbons ($C_5^+$) with a high content of non-aromatic compounds, and water, pass through line (3) into the first working up stage (4).

Borosilicate zeolites of the pentasil type are particularly suitable catalysts for this first stage. The reaction products from the first stage are removed in (4) in a conventional manner. After the $C_2$–$C_4$-olefins and $C_1$–$C_4$-paraffins and the water have been removed by a product line (5), through which they are passed for further separation, the $C_5^+$ hydrocarbons pass via line (6) into the second reactor (7), where they are reacted again over a zeolite catalyst. In this case also, borosilicate zeolites are advantageously used as catalysts. This reaction can be carried out in the presence of a diluent, preferably water, in a ratio of from 1:2 to 2:1, or in the absence of a diluent. In this case the water does not have to be removed in (4). The hydrocarbons obtained in reactor (7) pass through line (8) into the second working up stage (9), where they are freed from the aromatics in a conventional manner, and from there are passed via line (10) to the reaction products from the first stage in (4). The recycled mixture contains $C_2$–$C_4$-olefins, $C_1$–$C_4$-paraffins and $C_5^+$ aliphatics. In an alternative embodiment, only ethylene and propylene are removed in working up stage (4), and the $C_5^+$ hydrocarbons, together with $C_1$–$C_4$-paraffins, butenes and water, are passed through line (6) into the second reactor (7). The aromatics removed in (9) are taken off via line (11).

The preparation of the preferred catalyst is described below:

A borosilicate zeolite is precipitated or crystallized by hydrothermal synthesis from 66.1 g of $SiO_2$ (Aerosil 200) and 30.85 g of $H_3BO_3$ in 881 g of an aqueous propane-1,3-diamine solution (a 50:50 mixture), and is dried at 170° C. for 24 hours and calcined at 500° C. for 24 hours. This borosilicate zeolite is composed of 91.2% of $SiO_2$, 4.74% of $B_2O_3$ and 0.015% of $Na_2O$. Mixing the zeolite with boehmite, in a ratio of 60:40, followed by extrusion, gives the catalyst used in the experiments described below.

Table 1 shows the results of the first stage of the process described below:

Crude methanol is converted into hydrocarbons over the above catalyst at various temperatures and throughputs in an isothermal V2A steel coil reactor of internal diameter 0.6 cm and length 90 cm. The reaction conditions and yields, based on the $CH_2$ employed, are shown in Table 1.

TABLE 1

| | Experiment | | | | |
|---|---|---|---|---|---|
| | 1 | 2 | 3 | 4 | 5 |
| Temperature | 400° C. | 375° C. | 400° C. | 450° C. | 500° C. |
| WHSV | 3.9 h$^{-1}$ | 7.8 h$^{-1}$ | 7.8 h$^{-1}$ | 7.8 h$^{-1}$ | 7.8 h$^{-1}$ |
| $CH_4$ | 1.3% | 0.6% | 1.0% | 2.4% | 3.7% |

TABLE 1-continued

|  | Experiment | | | | |
|---|---|---|---|---|---|
|  | 1 | 2 | 3 | 4 | 5 |
| $C_2H_4$ | 5.3% | 5.4% | 5.5% | 7.1% | 9.5% |
| $C_2H_6$ | 0.2% | 0.1% | 0.1% | 0.2% | 0.3% |
| $C_3H_6$ | 15.9% | 13.0% | 18.1% | 31.3% | 36.9% |
| $C_3H_8$ | 2.5% | 2.4% | 2.2% | 1.4% | 1.2% |
| $C_4H_8$ | 16.1% | 15.1% | 16.4% | 18.0% | 16.8% |
| $C_4H_{10}$ | 7.8% | 2.0% | 8.2% | 3.9% | 2.0% |
| $C_5^+$ | 50.8% | 60.7% | 48.2% | 35.5% | 29.0% |
| of these | | | | | |
| BTX aromatics | 7.2% | 6.7% | 6.3% | 5.7% | 8.4% |
| g of $CH_3OH$/g of calyst+ | 350 g | 312 g | 413 g | 375 g | 218 g |

+running time until the first regeneration

A representative $C_5^+$ fraction such as is obtained from the first phase of the process after the $C_2$-$C_4$-olefins have been removed consists of 75.7% by weight of aliphatics and 24.3% by weight of aromatics. This mixture is converted into lower olefins in the $C_2$-$C_4$-range over the borosilicate catalyst, with and without the addition of water. The experimental results are summarized in Table 2:

TABLE 2

| Example | (no addition of $H_2O$) | (addition of $H_2O$) |
|---|---|---|
| Temperature | 500° C. | 500° C. |
| WHSV | 4.7 h$^{-1}$ | 4.8 h$^{-1}$ |
| $C_5^+$ : $H_2O$ | — | 50%:50% |
| Conversion of the $C_5^+$ aliphatics | 39.7% | 49% |
| Selectivity for gaseous $C_1$-$C_4$ products | 56.3% | 79.4% |
| Selectivity for aromatics | 43.7% | 20.6% |
| Selectivity for the individual gaseous components | | |
| $CH_4$ | 0.6% | 0.3% |
| $C_2H_4$ | 8.9% | 14.0% |
| $C_2H_6$ | 0.9% | 0.5% |
| $C_3H_6$ | 21.7% | 37.9% |
| $C_3H_8$ | 5.3% | 3.3% |
| $C_4H_8$ | 14.2% | 15.5% |
| $C_4H_{10}$ | 4.5% | 7.6% |

The experiments in Table 2 show that the overall yield of lower olefins can be increased by conversion of the $C_5^+$ aliphatics in a second reaction stage, and the selectivity of the catalyst for gaseous $C_1$-$C_4$ products is increased by adding $H_2O$.

We claim:

1. A two-stage process for the preparation of lower olefins from methanol and/or dimethyl ether by catalytic conversion at from 300°-550° C. in the presence of zeolite catalysts, wherein the selectivity for $C_5^+$ hydrocarbons is suppressed and the overall selectivity for $C_1$-$C_4$ hydrocarbons is optimized, which comprises; reacting methanol and/or dimethyl ether over borosilicate zeolite catalyst at from 300°-550° C. in a first reaction stage, removing $C_2$ and $C_3$ olefins after the first reaction stage in a working-up stage as gas, passing the remaining $C_4$ olefins, $C_1$-$C_4$ paraffins and liquid reaction mixture to a second reaction stage, reacting the remaining hydrocarbons in the second reaction stage at from 300°-550° C. over borosilicate zeolite catalyst, removing aromatics from the product of the second reaction stage, and recycling the remaining reaction product to the working-up stage.

2. A two-stage process for the preparation of lower olefins from methanol and/or dimethyl ether by catalytic conversion at from 300°-550° C. in the presence of zeolite catalysts, wherein the selectivity for $C_5^+$ hydrocarbons is suppressed and the overall selectivity for $C_1$-$C_4$ hydrocarbons is optimized, which comprises; reacting methanol and/or dimethyl ether over borosilicate zeolite catalyst at from 300°-550° C. in a first reaction stage, removing $C_2$-$C_4$ olefins, and $C_1$-$C_4$ paraffins after the first reaction stage in a working-up stage as gas, passing the remaining liquid reaction mixture to a second reaction stage, reacting the remaining hydrocarbons in the second reaction stage at from 300°-550° C. over borosilicate zeolite catalyst, removing aromatics from the product of the second reaction stage, and recycling the remaining reaction product to the working-up stage.

3. A process as claimed in claim 2, wherein, after removal of the aromatics, the reaction product from the second stage is recycled to the working up stage which follows the first reaction, and the $C_2$-$C_4$-olefins contained in the product are removed in this working up stage, together with the $C_2$-$C_4$-olefins from the first reaction stage, and the remaining hydrocarbons are passed to the second reaction stage.

4. A two-stage process for the preparation of lower olefins, as recited in claim 2, wherein water of reaction is removed with the $C_2$-$C_4$ olefins and $C_1$-$C_4$ paraffins following the first reaction stage.

5. A two-stage process as recited in claim 2, wherein the zeolite catalyst present in the first reaction stage is a borosilicate zeolite of the pentasil type.

6. A two-stage process as recited in claim 5, wherein the temperature in the first reaction stage is 350°-425° C., whereby the formation of $C_5^+$ hydrocarbons is suppressed and catalyst life is optimized.

7. A two-stage process as recited in claim 2, wherein the temperature in both reaction stages is 350°-425° C., whereby the formation of $C_5^+$ hydrocarbons is suppressed and catalyst life is optimized.

8. A two-stage process as recited in claim 2, wherein the reaction mixture in the second reaction stage contains a diluent in a weight ratio of from 1:2 to 2:1 diluent to reactants.

9. A two-stage process as recited in claim 8, wherein the diluent comprises water.

10. A two-stage process as recited in claim 2, wherein the catalyst is a borosilicate zeolite prepared by reacting $SiO_2$ and $H_3BO_3$ in an aqueous propane-1,3-diamine solution to form a zeolite, drying the crystalline product, calcining the dried zeolite, and mixing the calcined zeolite with boehmite in a ratio of 60:40, respectively, and extruding the mixture.

* * * * *